United States Patent [19]

Maeda et al.

[11] Patent Number: 4,954,340
[45] Date of Patent: Sep. 4, 1990

[54] METHOD FOR ACTIVATING HEMOCYTES OF BIVALVES FOR PEARL PRODUCTION

[75] Inventors: Haruhisa Maeda, Kumamoto; Akira Tsujikawa, Hondo; Sadao Susumi, Kumamoto, all of Japan

[73] Assignee: Juridical Foundation The Chemo-Sero-Therapeutic Research Institute, Kumamoto, Japan

[21] Appl. No.: 227,400

[22] Filed: Aug. 2, 1988

[30] Foreign Application Priority Data

Apr. 23, 1988 [JP] Japan ................. 63-100979

[51] Int. Cl.$^5$ ............ C01F 11/18; A61K 35/56; A61K 39/02
[52] U.S. Cl. .................. 424/92; 424/88; 424/93; 424/195.1; 424/520; 514/8
[58] Field of Search ............ 424/88, 92, 93, 195.1; 514/8

[56] References Cited

U.S. PATENT DOCUMENTS

| 3,975,517 | 8/1976 | Wilson | 424/92 |
| 4,123,427 | 10/1978 | Daniel | 530/389 |
| 4,470,967 | 9/1984 | Gough et al. | 424/89 |
| 4,755,382 | 7/1988 | Flaherty | 424/92 |
| 4,789,544 | 12/1988 | Nelson et al. | 424/92 |

FOREIGN PATENT DOCUMENTS 1942161 2/1970 Fed. Rep. of Germany ........ 424/93

OTHER PUBLICATIONS

"Treatment of Piece with Chemicals"—Effect of Pincchloron, Pearlthin and Pearlap—, by A. Machii (National Pearl Res. Lab.), pp. 1–7.
Boivin et al., "Recherches Sur Les Antigenes Somatiques Deu Bacille Typhique", Comp. Rend. Soc. Biol., vol. 128, pp. 5–8 (1938).
Boivin et al., "Technique Por La Preparation Des Polysacchardies Microbiens Specifiques", Comp. Rend. Soc. Biol., vol. 113, pp. 490–492 (1933).
"Seibutsugakuteki Seizai Kijun", pp. 57–59 (1985).
"Kaiyo Seibutugaku", Marine Biology, pp. 227–228 (1968).
Umemoto et al., "Shinju no Yoshoku", pp. 29–30 (1987).
Westphal et al., "Uber die Extraktion von Bakterien mit Phenol/Wasser", Z. Naturforsch, 7B, pp. 148–154 (1952).

*Primary Examiner*—Jacqueline Stone
*Assistant Examiner*—Jean Witz
*Attorney, Agent, or Firm*—Fleit, Jacobson, Cohn, Price, Holman & Stern

[57] ABSTRACT

A preparation for activating hemocytes of bivalves for pearl production containing a mitogen as an effective component, and a method for producing pearl through nucleus insertion operation of a bivalve for pearl production which comprises treating a section of the mantle part of a donor to be inserted with a mitogen.

By the treatment with the present preparation, hemocytes of the wound site due to the nucleus insertion operation are activated, tissue growth of the section of the mantle part of the donor is accelerated and a good pearl sac is formed around the nucleus. As a result, the number ejected nuclei is decreased and the pearl quality and production amount are enhanced.

These effects are further enhanced by using a mitogen treated with an aluminum adjuvant or the like.

16 Claims, No Drawings

METHOD FOR ACTIVATING HEMOCYTES OF BIVALVES FOR PEARL PRODUCTION

BACKGROUND OF THE INVENTION

1. Field of the Invention

The invention relates to preparations for activating hemocytes of bivalves for pearl production used in nucleus insertion operation in culture pearl production, and a method for producing pearls using such a preparation. The invention provides a useful and new technique for productivity enhancement in the industry of pearl culture.

More specifically, preparations obtained by the invention activate hemocytes at the wound site by the nucleus insertion operation on bivalves for pearl production, and thereby promote tissue growth of a section of the mantle of a donor, which is another pearl oyster, (this section is hereinafter referred to as a "piece") after this piece is inserted together with the nucleus to form a good pearl sac around the nucleus. Therefore, by use of the preparations, the pearl production yield is improved.

The technique of culturing of pearls was first established in Japan and developed as an important industry peculiar to Japan. This technique has recently spread abroad, for example, to Southeast Asia.

The nucleus insertion operation, which is an important step in production of cultured pearls, is carried out by incising the gonad part of a bivalve such as pearl oyster (*Pinctada martensii*), goldlip (*Pinctada maxima*) or pearly freshwater mussel (*Hyriopsis schleqeli*), and inserting therein in mutually close contact (1) a spherical nucleus prepared by processing a shell, for example, a thick shell of a freshwater shellfish from the USA, and (2) a square piece prepared by cutting out a 2 to 3 mm square mantle part of a donor.

Granular hemocytes (granular blood cells) and agranular hemocytes (agranular blood cells) exist in a floating state as so-called blood cells in the humor of shellfishes, and are considered to play a role similar to the role of macrophages and lymphocytes in vertebrates. These cell groups are called hemocytes or wandering cells in invertebrates, and the humor thereof is thought of as blood.

Hemocytes, particularly agranular hemocytes, assemble along the inside of the incised part wherein the nucleus is inserted, by nucleus insertion operation, and a sheet formed of the hemocytes is formed on the surface of the nucleus. The tissue cells of the piece proliferate by division along this sheet, gradually surround the nucleus to form a pearl sac, and secrete nacreous substantia inside the pearl sac, whereby a nacreous layer is formed on the surface of the nucleus. The object of the piece insertion is to form a pearl sac so as to cause nacreous substantia to be secreted on the surface of this nucleus.

As will be understood from the foregoing, the more rapidly the hemocytes assemble at the topical site of the nucleus insertion operation and the sooner the operation wound heals, the higher is the likelihood of a pearl sac being formed. At the same time, the rate of pearl production is increased and productivity is enhanced. It is important in pearl culturing to carry out these steps at low cost and with good reproducibility, and development of techniques enabling this has been greatly desired.

2. Prior Art

Many factors have an influence on pearl quality. For example, lack of close contact of the piece with the nucleus at the time of the nucleus insertion operation may become a cause of formation of a shiradama (a nucleus lacking nacreous layer) or a kuzudama (a nucleus only partially coated with nacreous substantia), neither of which has any commercial value. For facilitating confirmation of this close contact, it has long been the practice to dye the piece using a diluent of mercurochrome, actizol, Eosine Y, food red or the like with sea water.

Further, various attempts have been made at producing pearls of a high quality by utilizing a pharmacological effect. For example, yolk lecithin, light sensitive dye agents, antibiotics, etc. may be used for the purpose. Yolk lecithin is said to activate the cells, light-sensitive dye agents have physiological activities such as a cell-activating activity, an activity accelerating healing of wound and a sterilizing activity, and antibiotics are used mainly for utilizing their sterilizing and bacteriostatic activities.

As practical examples of a preparation containing a light-sensitive dye agent as a main component, there can be mentioned Praxin (manufactured by KK Nippon Kanko Shikiso Kenkyusho) wherein Pratonin and Neoxin are compounded, and Minol No. 1 (manufactured by KK Nippon Kanko Shikiso Kenkyusho). As antibiotics, aureomycin, chlorotetracycline, etc. are used. Further, azomine (Heiwa Seiyaku KK), which uses an azo dye, has been marketed. Azomine is a preparation consisting of sodium sulfothielazonaphtoldisulfonic acid and p-aminophenylsulfonamide as azo dyes which provide sterilizing or antiphlogistic activities, compounded together with sodium salt of chondroitin sulfate or taurine as a cell-activating agent. In addition to providing pharmacalogical effect, it also dyes the piece with the azo dye.

All of these preparations now on the market are diluted to predetermined concentration with sea water at the time of use and are then. supplied onto the piece, for example, by using a dropper to drop the dilution on the piece cut into smaller pieces, applying the dilution with a brush or the like onto a piece cut into smaller pieces, or immersing the whole piece in the dilution before it is cut.

Examples of known effective techniques are cited below. These are taken from Uemoto, et al., "Shinju no Yoshoku" (Pearl Culture) published by Nippon Shinju Shinko Kai, Tokyo, PP 29-30 (1987). Takaoka (1957) is reported as saying that an effect was brought about by methionine and that Illuminol RII gave a slightly higher emergence rate of pearls of good quality. Yamashita et al. (1961) are reported as saying that when Pratonin or Neoxin is used as a light-sensitive dye, the resulting pearls have few CH carrier, of flaws. Their view is based on only 2 or 3 shellfishes and is hard to evaluate due to the small number of experimental examples. Miyauchi (1962) is reported as saying that Eosine Y was more harmless and brought about higher emergence rate of higher grade pearls than mercurochrome, and that the emergence rate of higher grade pearls became higher, the rate of shiradama production became lower and further, the death rate after nucleus insertion was decreased by dyeing the piece with a mixed solution of chlorotetracycline and mercurochrome and further immersing the shellfish and an apparatus for inserting a nucleus in a chlorotetracycline solution before and after nucleus insertion. Machii (1965) is reported as having concluded that yolk lecithin, aureomycin and pincchloron were effective because better results, as respectively compared with the control group, were obtained in 12 groups among 20 test groups in case of yolk lecithin, in 8 groups among 14 groups in case of Aureomycin and 19 groups among 33 groups in case of pincchloron in experiments carried out several times using 100 to 300 shellfishes per group. However, Machii is also said to have noted that the rate of production of kizudama (a nucleus missing some of its nacreous substantia coating or having a protuberance(s); limited commercial value) and kuzudama became higher in many groups. Further, Machii (1967) is said to have found that using yolk lecithin and pincchloron together, and using yolk lecithin and aureomycin together were both effective, and to have stated of that in such cases, though the number of kizudama and kuzudama were not decreased, the problem of increase in the number of kuzudama due to phytotoxicity was eliminated.

Further, there is a disclosure that the productivity of good quality pearls was higher in pearls of the azomine-treated group as harvested than in pearls of the control group as harvested, but it is not certain whether the disclosure is credible.

From the poor results obtained by their actual use in the field, these preparations cannot be expected to increase productivity substantially, and thus enhancement of the yield of good quality pearls is desired. It is necessary for formation of a pearl sac that tissue division of the inserted piece occur regularly, and it is a prerequisite for this that many of the agranular blood cells in the shellfish body assemble around the inserted nucleus and smoothly surround the nucleus. Thus, it is necessary to form a good pearl sac by activating the hemocytes and accelerating the activity of the piece.

SUMMARY OF THE INVENTION

From the foregoing viewpoint, it is desirable for practical application to further improve the conventional techniques. As is apparent from the foregoing, the known methods entail problems regarding the effects thereof, etc.

This invention has been accomplished based on the very interesting finding that mitogens known as a cytokinetic factor can be an active component which activates the hemocytes of bivalves for pearl production.

More specifically, the invention relates to preparations for activating the hemocytes of a bivalve for pearl production which contain a mitogen as an effective component.

DETAILED DESCRIPTION OF THE INVENTION

"Mitogen" is a general term for substances which induce and accelerate cytokinesis. Typically included among the mitogens are: lipopolysaccharides (hereinafter referred to as LPS) which exist widely as a cell wall-constituting component of Gram-negative bacteria; lectins contained in certain kinds of vegetable seeds; and purified protein derivatives (hereinafter sometimes referred to as PPD) derived from acid-fast bacteria such as tubercle bacillus. These materials have conventionally been used for biological and biochemical research because of the mitogenic and other biological activities thereof. All of these typical mitogens are commercially available as purified preparations.

Methods for obtaining LPS include the method of Westphal et al. wherein the cells are suspended in hot phenol water to extract LPS (Van Off Westphal et al., Z Naturforsch., 7B, 148-155 (1952)); the method of Boivin et al. wherein the cells are extracted with trichloroacetic acid (Boivin, A et al., Comp. Rend. Soc. Biol., 113, 490 (1933) and 128, 5 (1938): etc. The present inventors have found that hemocyte activating activity in bivalves for culture pearl production is exhibited by all LPS preparations prepared according to the above methods from cells of various Gram-negative bacteria such as Escherichia, Serratia, Salmonella, Shiqella, Vibrio and Pseudomonas, and that the LPS preparations can be widely used in the method of the invention. There are no specific culturing conditions which are indispensable for obtaining the cells used in obtaining LPS preparations.

PPD derived from acid-fast bacteria is a purified protein derivative obtained from the culture broth of *Mycobacterium tuberuculosis* in Sauton medium, and can be used in the method of the invention. Similar active substances can be obtained from other acid-fast bacteria as a PPD-like substance.

Lectins are mitogens derived from plants particularly from the seeds of leguminous plants, etc. Lectin is a general term for proteins which recognize a specific saccharide chain structure and link to it. These lectins can be purified, for example, by affinity chromatography using Sephadex as a specific carrier. Lectins have wide-ranging biological activities. Typical among lectins which accelerate the division of lymphocytes are concanavalin A (Con A) derived from horse bean, kidney bean lectin (PHA), phytolacca americana lectin (PWM) and agglutinin. All of these substances activate hemocytes of bivalves for culture pearl production, and can be used in the method of the invention with good results.

Other substances exhibiting the mitogen activity required in the invention to greater or lesser degrees include inactivated microorganism cells containing LPS and inactivated broth containing such cells. Any microorganism suitable for preparing LPS preparations, for example, various Gram negative bacteria such as Escherichia, Serratia, Salmonella, Shiqella, Vibrio, Pseudomonas can be used and there is no limitation to specific species. Further, any medium and any culturing method can be used for culturing these microorganisms so long as they are suitable for growth of the microorganism.

Interestingly, coexistence of an adjuvant substance is effective for further increasing the hemocyte-activating activity of mitogen according to the invention. Such aluminum adjuvants, as potash alum gel, aluminum hydroxide gel, and aluminum phosphate gel, are all effective as an adjuvant. Other substances exhibiting adjuvant activity can also be used. These include muramyldipeptide and various other substances having an immunity-increasing activity.

The effect of the invention is exhibited even by sole use of a mitogen, but is only slightly exhibited by sole use of an adjuvant substance. The most desirable activity is brought about by use of an adjuvant-treated mitogen.

Physiological saline, Ringer's solution, artificial sea water, etc. are preferably used as the liquid for suspension (liquid for dilution and preparation) used in preparation of activating preparations of the invention. Natural seawater can also be used therefor. Further, buffer solutions can also be used so long as they can control the pH to within the range of 5 to 7.

In the present invention, an LPS preparation is adjusted to a concentration of 0.5 to 100 ng/ml, preferably 10 to 50 ng/ml, a lectin preparation is adjusted to a concentration of 1 to 2,000 ng/ml, preferably 10 to 100ng/ml, a PPD preparation is adjusted to a concentration of 1 to 1,000 ng/ml, preferably 10 to 100 ng/ml, and an inactivated microorganism is adjusted to a concentration of $10^{6-9}$/ml, preferably $10^{7-8}$/ml, using a salt solution such as physiological saline or Ringer's solution, or a buffer solution. It is further desirable that an adjuvant treatment be carried out by addition of aluminum gel in the pH range of about 5 to 7.

It is adequate for the aluminum gel to be added to a concentration of 0.005 to 1mg/ml, preferably 0.01 to 0.1mg/ml in terms of $Al_2O_3$ as the final concentration.

When the preparation is made using an inactivated microorganism, the cells of a microorganism are, for example suspended in physiological saline, Ringer's solution, etc. to a predetermined cell concentration, and then either subjected to a heat treatment at a temperature of the order of 55° C. for one hour, or treated for about 30 minutes by the addition of formalin so as to make the concentration 5v/v%. With respect to the above procedures, any of the conventional methods for inactivation can be utilized.

When a suspension in Ringer's solution containing 10ng/ml LPS derived from *E. coli* and 0.03 mg/ml potash alum gel was used as preferred preparation in immersion treatment of a piece in a nucleus insertion operation on pearl oysters, it was found that the number of hemocytes contained in the blood at the topical wound site increased markedly. The number of hemocytes in most of the shellfishes reached a maximum 24 hours after the operation, and the number of hemocytes became 1.6 times or more that of untreated shellfishes. Also, with preparations from inactivated microorganisms, for example, an inactivated *V. alqinolyticus* cell suspension treated with potash alum gel, an increase of about 80% in hemocyte number was obtained. After peaking at 24 hours following the operation, the hemocyte number remained generally constant or decreased. It is considered that such activation of topical hemocytes accelerates the formation of a pearl sac.

These mitogens can be used not only individually but also in combination. For example, there can be used a combination of two or more LPS's and lectins or a combination of members selected respectively from LPS's, lecitins and PPD's. Similar combination of inactivated microorganisms is also possible.

The present preparations for industrial utilization should of course be aseptically prepared. The preparations can be preserved so as to maintain the desired activity for a long period if they are sealed in a proper vessel such as a vial under conventional preservation conditions in a cool and dark place. However, the preparations of the invention added with aluminum gel can be preserved in a frozen state, which is the usual case for aluminum gel-added preparations.

The mitogens and adjuvants, which are the main components of the present preparations, are desirably used in a purified state since this enables reproducibility of the quality of the preparations and provides preparations that are extremely stable in characteristics and state. The present preparations can be prepared on an industrial scale, and are able to respond to the requirements of the site of pearl culturing, regardless of time or place.

The action of mitogens and the mechanism thereof in mammal cells is known. Specifically, Con A, PHA, etc. stimulate T cells, LPS stimulates B cells, and PWM stimulates T and B cells. It is further known that when these mitogens are added to target lymphocytes in a test tube, followed by culturing, these lymphocytes change to large juvenile cells having divisional ability, and further, various lymphokines and monokines are produced and secreted in this step.

There are few known effects of mitogens on invertebrates, particularly on bivalves, including their hemocytes, and it has remained unclear whether or not mitogens have activities on them similar to those on mammal cells. The effect discovered by the inventors that hemocytes of pearl oyster, etc. are activated by mitogens such as LPS, lectins, PPD or inactivated microorganisms, and further that this effect is further increased by coexistence of adjuvants is considered to be a new finding.

As is clarified later in examples, the number of ejected nuclei is decreased and the quality and production amount of commercially valuable pearls are enhanced by utilization of the present preparations. Thus, the invention provides a useful method for producing pearls. It is expected that this method will greatly contribute to an increase in the productivity of pearl culturing.

The preparations of the invention are used for bivalves capable of producing pearls, and have no bad influence on the growth of the bivalves. Further, it has been demonstrated by a test regarding freedom from abnormal toxicity that there is no safety risk even if the present preparation leaks out into the natural environment. Namely, undiluted preparation solutions respectively comprising LPS derived from *E. coli* +potash alum, LPS derived from *V. alginolyticus* +potash alum, Con A+potash alum, or potash alum alone; or 10-fold diluted solutions thereof with a high concentration was intraperitoneally administered to rainbow trouts (body weight (BW), 5g), young yellowtails (BW 20g), ddY mice (BW 20g) and Hartley guinea pigs (BW 200g), each group consisting of 5 animals, in an amount of 0.2ml, 0.5ml, 0.5ml or 3.0ml, respectively. These animals together with animals of a control group to which none of the above preparations was administered were observed for 2 weeks. No abnormality was observed in body weight or other general aspects.

The present preparations utilize as a main component mitogens known to be normal constitutive components of microorganisms and plants in nature, and moreover the concentration and dose of these components necessary for exhibiting the effect of the invention are very low. Thus, it is believed that there is no problem about the safety of the preparations.

The present invention is further described below by examples, but is not be limited thereby.

EXAMPLE 1

Preparation of LPS (1) LPS was prepared by a method similar to that of Westphal et al. referred to earlier using *E. coli* cells cultured in an ordinary agar medium at 25° C. for 24 hours. Wet cells (10g) were extracted with 90w/v% hot phenol water and the extract was dialyzed against distilled water. The extract was then centrifuged at 100,000×g for 2 hours and the resulting precipitate was freeze-dried to obtain 12 mg as dry weight of LPS preparation.

(2) *Serratia marcescens* was cultured in the same manner as in Example 1-(1), and the resulting wet cells (10g) were treated in the same manner as in Example 1-(1) to obtain 18 mg as dry weight of LPS preparation.

(3) *V. alginolyticus* was cultured in a 2 w/v% sodium chloridecontaining ordinary bouillon medium at 25° C. for 24 hours. LPS was prepared from the cultured cells in a manner similar to that of Boivin et al. referred to earlier. Wet cells (5g) were extracted with an aqueous 0.5N trichloroacetic acid solution, and the extract was centrifuged at 6,000×g for 30 minutes. Ethanol ice-cooled to −15° C. was added to the supernatant and the mixture was allowed to stand overnight at −4° C. The mixture was then recentrifuged at 6,000×g for 30 minutes. The precipitate was washed with ethanol-ether and dissolved in distilled water, and dialyzed. The solution was further recentrifuged at 27,000 ×g for 30 minutes and the supernatant was freeze-dried to obtain 8 mg as dry weight of LPS preparation as white powder.

EXAMPLE 2

Preparation of a preparation for activating hemocytes of bivalves for pearl production (hereinafter referred to as the present preparation)

(1) LPS derived from *E. coli* as prepared in Example 1-(1) was dissolved in Ringer's solution (prepared by dissolving 8.6g of NaCl, 0.3g of KCl and 0.33g of $CaCl_2$ in 1000ml of purified water) to the concentrations of 1, 5, 100, 500, 1,000, 5,000, and 10,000 ng/ml, respectively. 10w/v% potash alum was added to each solution to a final concentration of 0.5w/v%, and the mixtures were adjusted to pH 0.5. The mixtures were centrifuged at 3,000 rpm for 20 minutes. The precipitates were respectively resuspended in ten times the amount of Ringer's solution as that first used to obtain the present preparation in 500 mg lots containing 0.1, 0.5, 10, 50, 100, 500, and 1,000 ng/ml LPS, respectively.

(2) 500 mg lots of the present preparation respectively containing 1, 10, 50 and 100 ng/ml of LPS derived from *V. alginolyticus* as obtained in Example 1-(3) were obtained in the same manner as in Example 2-(1).

Separately, the LPS was dissolved in 500 ml of Ringer's solution to 10 mg/ml, and aluminum hydroxide gel (2w/v% in terms of $Al_2O_3$) was added thereto with stirring to a final aluminum concentration of 0.03 mg/ml. The pH at the time of preparation was 5.8. There was obtained 500 ml of the present preparation containing 10 ng/ml LPS.

(3) LPS derived form *E. coli* as obtained in Example 1-(1) was aluminum hydroxide gel-treated in the same manner as in Example 2-(2) to obtain 100 ml of the present preparation containing as the final concentration 0.03 mg/ml aluminum and 10 mg/ml LPS. Separately, 100 ml of the present preparation containing as the final concentration 0.03 mg/ml aluminum and 10 ng/ml LPS was obtained by repeating the above procedure except that aluminum phosphate gel was used in place of aluminum hydroxide gel.

(4) Using LPS derived from *E. coli* as obtained in Example 1-(1), 100 ml lots of the present preparation were obtained by a procedure similar to Example 2-(1) except that physiological saline, PBS (prepared by dissolving 8.0g of NaCl, 0.2g of KCl, 1.15g of $Na_2HPO_4$ and 0.2g of $KH_2PO_4$ in this order in 1,000 ml of purified water) and artificial sea water (prepared by dissolving 26.75g of $CaCl_2$ in this order in 1,000ml of purified water; Kiyoharu Kokubo, "Kaiyo Seibutsugaku" (Marine Biology), pp. 227–228, published by Kosei Sha Koseikaku (Tokyo), 1968) were used respectively as a diluting and preparing solution for the present preparation in place of Ringer's solution.

(5) Con A, PHA and PWM purchased from Funakoshi Yakuhin Co., Ltd. were separately dissolved in Ringer's solution and the solutions were then subjected to a procedure similar to Example 2-(1) to obtain 500 ml lots of the present preparation containing the respective lectins.

(6) A procedure similar to that disclosed in "Seibutsugakuteki Seizai Kijun" (Biological Preparation Standard), compiled under the supervision of the Pharmaceutical Affairs Bureau, the Welfare Ministry, published by Saikin Seizai Kyokai (Tokyo), pp. 57 to 61 (1985) was carried out using the culture filtrate obtained by culturing *Mycobacterium tuberculosis* in Sauton medium to prepare freeze-dried tuberculin protein powder as PPD. The PPD was dissolved in Ringer's solution, followed by treatment according to Example 2-(1) to obtain 100 ml of the present preparation containing PPD.

(7) *V. alginolyticus* was cultured in an ordinary agar medium for 24 hours. The resulting cells were suspended in Ringer's solution to a cell concentration of $10^7$/ml and inactivated by heating at 55° C. for one hour. Potash alum was added to the cell suspension to an aluminum content of 0.03 mg/ml (in terms of $Al_2O_3$) for adjuvant treatment to obtain as the present preparation 500 ml of a cell suspension treated with potash alum wherein *V. alginolyticus* was inactivated by heating.

EXAMPLE 3

Application results

The results of applying the preparations of the invention are shown below. The test was carried out by immersing pieces in the present preparations respectively and then inserting two nuclei and two pieces per pearl oyster. 0.05 ml of the present preparation was used per piece. An untreated group was used as control. Measurement of hemocyte number was carried out according to a conventional method, namely by using a syringe to sample 0.1 ml of blood from near the inserted nuclei, diluting the sampled blood with Ringer's solution to 10 fold the sampled volume, and measuring hemocytes using a Burken-Turk Blood cell counting board. In each measurement, the total hemocyte number per 0.1 $mm^3$ of blood in each of 10 shellfishes from each group was determined and the average number is shown in Table 1.

(1) Change in the hemocyte number at the topical wound site was observed for the case of the present preparation according to Example 2-(1) and containing LPS derived from *E. coli*, and the case of the potash alum gel-treated and heating-inactivated *V. alqinolyticus* cell suspension prepared as the present preparation according to Example 2-(7). Reference tests were carried out using LPS alone or potash alum alone. Observation was carried out at 24, 48 and 72 hours after the operation.

The results were as shown in Table 1. As is apparent from this table, the hemocyte number in all test groups were higher than in the untreated control group. This tendency was particularly pronounced in the test groups in which the present preparations were used.

TABLE 1

Topical hemocyte number after the nucleus insertion operation

| Group | Time Elapsed after operation | | |
|---|---|---|---|
| | 24 hr | 48 hr | 72 hr |
| LPS derived from *E. coli* 10 ng/ml | 1,199 | 1,127 | 1,065 |
| Alum gel | 1,144 | 1,225 | 1,103 |
| "LPS derived from *E. coli* 0.1 ng/ml Alum gel" | 1,216 | 1,181 | 916 |
| 0.5 ng/ml + Alum gel" | 1,376 | 1,285 | 1,131 |
| 10 ng/ml + Alum gel" | 1,511 | 1,478 | 1,284 |
| 50 ng/ml + Alum gel" | 1,658 | 1,397 | 1,509 |
| 100 ng/ml + Alum gel" | 1,701 | 1,481 | 2,072 |
| 500 ng/ml + Alum gel" | 1,568 | 1,218 | 1,241 |
| 1,000 ng/ml + Alum gel" | 1,476 | 1,366 | 1,800 |
| *V. alginolyticus* cell suspension + Alum gel | 1,217 | 1,345 | 1,685 |
| Control | 1,075 | 1,091 | 882 |

(2) The effect of the various adjuvants on the topical hemocyte number after the nucleus insertion operation was investigated for the case of the present preparation prepared according to Example 2-(3) and containing LPS derived from *E. coli*, and the case of the potash alum gel-treated and heating-inactivated *V. alginolyticus* cell suspension prepared as the present preparation according to Example 2-(7).

As is apparent from the results shown in Table 2, the hemocyte number at 24 hours after the operation in the test groups were larger than that in the control group, and this tendency was observed for all adjuvants This tendency was not clearly observable at 48 and 72 hours Examples 3-(1) and 3-(2) show that the effect of the present preparations can most rapidly and accurately be estimated by measuring the hemocyte number 24 hours after the operation. Therefore, only the results at 24 hours are shown for the remaining tests discussed herein.

TABLE 2

Topical hemocyte number after the nucleus insertion operation

| Group | Time Elapsed after operstion | | |
|---|---|---|---|
| | 24 hr | 48 hr | 72 hr |
| LPS derived from *E. coli* 10 ng/ml + Alum gel | 1,105 | 892 | 918 |
| LPS derived from *E.coli* 10 ng/ml + Aluminum hydroxide gel | 1,250 | 913 | 946 |
| LPS derived from *E. coli* 10 ng/ml + Alum phosphate gel | 1,273 | 851 | 917 |
| *V. alginolyticus* cell suspension + Alum gel | 1,115 | 905 | 931 |
| Control | 976 | 717 | 1,017 |

(3) The effect of the various solutions for dilution and preparation on the topical hemocyte number after the nucleus insertion operation was investigated for the case of the present preparation prepared according to Example 2-(4) and containing LPS derived from *E. coli*. The solution of potash alum-gel alone in the control test group was prepared using Ringer's solution.

As is apparent from the results shown in Table 3, the hemocyte numbers in all the test groups were larger than that in the control section, and thus the solutions for dilution and preparation can be used as those for the present preparations.

TABLE 3

Topical hemocyte number after the nucleus insertion operation

| Group | Time Elapsed after operation 24 hr |
|---|---|
| LPS derived from *E. coli* 10 ng/ml + Alum gel | |
| Ringer's solution | 1,227 |
| Physiological saline | 1,443 |
| PBS | 1,058 |
| Artificial sea water | 1,287 |
| Alum gel | 1,017 |
| Control | 929 |

(4) The effect of the present preparations prepared using LPS derived from various Gram-negative bacteria on the topical hemocyte number after the nucleus insertion operation was investigated. The present preparations (1) and (5) referred to in Table 4 are those prepared according to Example 1-(1) and 2-(2), respectively. The present preparations (2), (6) and (7) were newly prepared using LPS obtained according to Example 1-(2), and the present preparations (3) and (4) were newly prepared using commercially available LPS (manufactured by Difco Co.).

As is seen from the results shown in Table 4, the hemocyte numbers in all the test groups were larger than that in the control group, and thus all the LPS's can be used for preparation of the present preparations.

TABLE 4

Topical hemocyte number after the nucleus insertion operation

| Group | Time Elapsed after operation 24 hr |
|---|---|
| (1) *Escherichia coli* | 1,048 |
| (2) *Serratia marcescens* | 1,136 |
| (3) *Salmonella enteritidis* | 1,211 |
| (4) *Shigella flexneri* | 1,049 |
| (5) *Vibrio alginolyticus* | 1,171 |
| (6) *Vibrio parahaemolyticus* | 1,248 |
| (7) *Pseudomonas aeruginosa* | 1,163 |
| Control | 915 |

LFS derived from the above microorganisms 10 ng/ml + Alum gel (5) The effect of the present preparations prepared using PPD and various lectins on the topical hemocyte number after the nucleus insertion operation was investigated. The present preparations were those prepared according to Examples 3-(5) and (6).

As is seen from the results shown in Table 5, the hemocyte number in all the test groups were larger than that in the control group, and thus the PPD and the various lectins can be used for preparation of the present preparations.

TABLE 5

Topical hemocyte number after the nucleus insertion operation

| Group | Time Elapsed after operation 24 hr |
|---|---|
| PPD 100 ng + Alum gel | 1,602 |
| Con A 100 ng + Alum gel | 1,541 |
| Con A 1000 ng + Alum gel | 1,681 |
| PHA 100 ng + Alum gel | 1,570 |
| PWM 100 ng + Alum gel | 1,521 |
| LPS derived from *E. coli* 10 ng/ml + Alum gel | 1,804 |
| Alum gel | 1,414 |

TABLE 5-continued

Topical hemocyte number after the
nucleus insertion operation

| Group | Time Elapsed after operation 24 hr |
|---|---|
| Control | 1,085 |

(6) Nucleus insertion operation was carried out on 100 per group of the shellfishes using the present preparations prepared according to Examples 2-(1) and (3) and containing LPS derived from *E. coli*. Twenty-five days after the nucleus insertion, test opening (opening to determine pearl quality) was conducted for comparison of quality and amount of the recovered pearls. The pearls were classified into flawless pearls, pearls with one flaw and pearls with large flaws and the numbers of each type were counted.

As is seen in Table 6, the results in all the test groups were better than that in the control group. More specifically, there were obtained more flawless pearls and fewer pearls with large flaws in the test groups. Further in the test groups the number of ejected nuclei was smaller and the total number of pearls is larger. Moreover, even in comparison of yield rate of nucleus insertion, the results in the test groups exceeded those in the control group.

The yield rate was calculated as follows. First, the total value of the recovered pearls was calculated presuming the value of each flawless pearl to be 200 yen, each pearl with one flaw to be 50 yen, and each pearl with large flaws to be 10 yen. Then this total value was divided by the total number of the shellfishes opened to find the average value per shellfish. The result was defined as the yield rate. The yield rate was similarly calculated in the remaining examples set out herein.

TABLE 6

Comparison of pearl quality by test opening

| Group | No flaw | One flaw | Large flaws | Total | Yield rate: yen/shellfish |
|---|---|---|---|---|---|
| *E. coli* LPS | | | | | |
| 1 ng/ml + Alum gel | 52 | 52 | 41 | 145 | 129 |
| 10 ng/ml + Alum gel | 39 | 45 | 66 | 150 | 103 |
| 50 ng/ml + Alum gel | 44 | 68 | 52 | 164 | 125 |
| 10 ng/ml + Aluminum hydroxde gel | 37 | 68 | 53 | 158 | 112 |
| Control | 22 | 34 | 72 | 128 | 66 |

(7) Nucleus insertion operation was carried out on 100 shellfishes per group using the present preparation prepared according to Example 2-(1) and containing LPS derived from *E. coli*, and the potash alum gel-treated and heating-inactivated *V. alginolyticus* cell suspension prepared as the present preparation according to Example 2-(7). Test opening was carried out 21 days after nucleus insertion and the quality and amount of the recovered pearls were compared.

As is apparent from Table 7, the results in all the test groups exceeded those in the control group.

TABLE 7

Comparison of pearl quality by test opening

| Group | No flaw | One flaw | Large flaws | Total | Yield rate: yen/shellfish |
|---|---|---|---|---|---|
| *E. coli* LPS 10 ng/ml + Alum gel | 47 | 67 | 50 | 164 | 129 |
| *V. alginolyticus* cell suspension + Alum gel | 34 | 79 | 47 | 160 | 112 |
| Control | 22 | 56 | 88 | 158 | 80 |

(8) Nucleus insertion operation was carried out on 100 shellfishes per group using the present preparation prepared according to Example 2-(2) and containing LPS derived from *V. alqinolyticus*, and the potash alum gel-treated and heating-inactivated *V. alginolyticus* cell suspension prepared as the present preparation according to Example 2-(7). Test opening was carried out 27 days after the nucleus insertion and the quality and amount of the recovered pearls were compared.

As is seen in Table 8, the number of flawless pearls in all test groups using the present preparations was larger than that in the control test group and control group, and moreover the yield rate of the nucleus insertion in the former groups exceeded that in the latter groups.

TABLE 8

Comparison of pearl quality by test opening

| Group | No flaw | One flaw | Large flaws | Total | Yield rate: yen/shellfish |
|---|---|---|---|---|---|
| *V. alginolyticus* LPS | | | | | |
| 1 ng/ml + Alum gel | 38 | 32 | 39 | 109 | 91 |
| 10 ng/ml + Alum gel | 44 | 43 | 43 | 130 | 109 |
| 50 ng/ml + Alum gel | 46 | 32 | 48 | 126 | 107 |
| 10 ng/ml + Aluminum hydroxide gel | 45 | 45 | 43 | 133 | 112 |
| *V. alginolyticus* cell suspension + Alum gel | 28 | 46 | 56 | 130 | 83 |
| Control | 27 | 33 | 55 | 115 | 73 |

(9) The effect of the present preparation prepared according to Example 2-(5) and containing Con A was compared with that of the solution containing potash alum gel alone in the control test group. Nucleus insertion operation was carried out using 100 shellfishes per group. Test opening was carried out 22 days after the nucleus insertion, and the quality and amount of the recovered pearls were compared.

As is seen in Table 9, the results in all the test groups exceeded those in the control test group and control group.

TABLE 9

Comparison of pearl quality by test opening

| Group | No flaw | One flaw | Large flaws | Total | Yield rate: yen/shellfish |
|---|---|---|---|---|---|
| Con A 100 ng/ml + Alum gel | 37 | 40 | 55 | 132 | 96 |
| Con A 1000 ng/ml + Alum gel | 33 | 48 | 50 | 131 | 93 |
| Alum gel | 29 | 58 | 53 | 140 | 91 |
| Control | 29 | 34 | 63 | 126 | 78 |

(10) Effect of the present preparation prepared according to Example 2-(1) and containing LPS derived from *E. coli* was investigated in terms of the harvest results. Nucleus insertion operation was carried out using 10,000 shellfishes per group. Harvest was conducted 157 days after the nucleus insertion, and the quality, amount and yield of the recovered pearls were determined and compared. The pearls were classified into 5 grades: high, middle, low, shiradama and kuzudama. Evaluation was conducted by grade and further by size (6 mm or 5mm).

The results are shown in Table 10. The number of surviving nucleus-inserted shellfishes was 78.9% for the test group and 79.8% for the control group and thus there was almost no difference between them. However, as for the recovered pearls, the number of high grade pearls was 4,545 and the total number of high grade pearls +middle grade pearls +low grade pearls was 11,346 in the test group, whereas the number of high grade pearls was 3,376 and the total number of high grade pearls + middle grade pearls +low grade pearls was 10,398 in the control group. It is particularly notable that the number of high grade pearls, which bring a high price, was much larger in the test group than that in the control group, and the difference was extremely significant.

Further, for comparing productivity, the nucleus insertion yield rate was calculated assuming a unit market price of 3,000 yen for 6 mm high grade pearls, 1,500 yen for 5 mm high grade pearls, 1,000 yen for 6 mm middle grade pearls and 500 yen for 5 mm middle grade pearls. On this basis, the yield rate was 156 yen in the test group and 107 yen in the control group, and thus there was an enhancement of productivity and a decrease in the number of ejected nuclei.

TABLE 10

| | | Comparison of quality of harvested pearls (*E. coli* LPS 10 ng/ml + Alum gel) | | | | | | |
|---|---|---|---|---|---|---|---|---|
| | | Quality grade | | | | | Total | |
| | Size (mm) | high | middle | low | shira dama | kuzu dama | high + middle | high + middle + low |
| Test | 6 | 0.47 (476) | 0.44 (429) | | | | 0.09 (905) | |
| Group | 5 | 0.11 (48) | 0.12 (95) | | | | 0.23 (143) | |
| | subtotal | 0.58 (524) | 0.56 (524) | 0.3 (286) | 0.08 | 0.09 | 1.14 (1,048) | 1.44 (1,334) |
| Control | 6 | 0.28 (274) | 0.37 (329) | | | | 0.65 | |
| Group | 5 | 0.14 (110) | 0.07 (55) | | | | 0.21 | |
| | subtotal | 0.42 (384) | 0.44 (384) | 0.44 (440) | 0.11 | 0.1 | 0.86 (768) | 1.3 (1,208) |

(11) Effect of the present preparation prepared in Example 2-(5) and containing Con A was investigated in terms of harvest results. Nucleus insertion operation was carried out using 10,000 shellfishes per each group. Harvesting was conducted 117 days after the nucleus insertion, and the quality, amount and yield of the pearls were determined and compared in the same manner as in Example 3-(10).

The results are shown in Table 11. The number of high grade pearls and the total number of high grade pearls +middle grade pearls +low grade pearls in the test group was larger than those in the control group, and the effect of reducing the number of ejected nuclei was also demonstrated.

TABLE 11

| | Comparison of quality of harvested pearls | |
|---|---|---|
| | Quality grade | |
| | high | high + middle + low |
| Test group | 3,878 | 11,411 |
| Control group | 3,269 | 10,971 |

What is claimed is:

1. A method for producing a pearl by a nucleus insertion operation including the step of inserting a nucleus and a section of a mantle part of a donor bivalve into a bivalve capable of producing a pearl, characterized by the step of applying a mitogen selected from the group consisting of lipopolysaccharides, lectins, purified protein derivatives derived from acid-fast bacteria and inactivated microorganisms containing lipopolysaccharides to the section of the mantle part of the donor bivalve to be inserted.

2. The method of claim 1 wherein the mitogen is a lipopolysaccharide obtained from a Gram-negative bacterium.

3. A method of claim 1 wherein the mitogen is a lectin.

4. A method of claim 3 wherein the lectin is concanavalin A(Con A) derived from horse bean, kidney bean lectin, phytolacca americana lectin or agglutinin.

5. A method of claim 1 wherein the mitogen is a purified protein derivative derived from acid-fast bacteria.

6. A method of claim 5 wherein the purified protein derivative is derived from tubercle bacillus.

7. A method of claim 1 wherein the mitogen is a lipopolysaccharide-containing inactivated microorganism.

8. The method of claim 1 wherein the mitogen is applied together with an adjuvant.

9. The method of claim 8 wherein the adjuvant is an aluminum adjuvant.

10. The method of claim 1 wherein the mitogen is applied by immersing the section of the mantle part of the donor bivalve in a mitogen-containing solution or suspension.

11. The method of claim 8 wherein the mitogen is applied by immersing the section of the mantle part of the donor in a solution or suspension containing a mitogen and an adjuvant.

12. A method of claim 10 wherein the mitogen-containing solution or suspension comprises a salt solution or a buffer.

13. A method of claim 10 wherein the mitogen-containing solution or suspension contains 0.5 to 100 ng/ml of a lipopolysaccharide, 1 to 2,000 ng/ml of a lectin, 1 to 1,000 ng/ml of a purified protein derivative derived from an acid-fast bacterium, or $10^{6-9}$/ml of a lipopolysaccharide-containing inactivated microorganism.

14. A method of claim 11 wherein the adjuvant is an aluminum gel.

15. A method of claim 14 wherein the solution or suspension contains the aluminum gel in an amount of 0.005 to 1 ng/ml in terms of $Al_2O_3$.

16. A method of claim 1 wherein the bivalve capable of producing a pear is a pearl oyster, goldlip or pearl fresh-water mussel.

* * * * *